(12) United States Patent
Liu et al.

(10) Patent No.: US 11,646,424 B2
(45) Date of Patent: May 9, 2023

(54) LITHIUM-ION SECONDARY BATTERY

(71) Applicant: Contemporary Amperex Technology Co., Limited, Ningde (CN)

(72) Inventors: Xin Liu, Ningde (CN); Qisen Huang, Ningde (CN); Shiwen Wang, Ningde (CN); Xianghui Liu, Ningde (CN); Jia Peng, Ningde (CN); Mingling Li, Ningde (CN); Changliang Sheng, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

(21) Appl. No.: 17/123,268

(22) Filed: Dec. 16, 2020

(65) Prior Publication Data

US 2021/0143440 A1    May 13, 2021

Related U.S. Application Data

(63) Continuation of application No. PCT/CN2019/090407, filed on Jun. 6, 2019.

(30) Foreign Application Priority Data

May 31, 2019    (CN) .......................... 201910473216.2

(51) Int. Cl.
*H01M 4/66* (2006.01)
*H01M 4/587* (2010.01)
(Continued)

(52) U.S. Cl.
CPC ........... *H01M 4/667* (2013.01); *C07C 317/12* (2013.01); *H01M 4/133* (2013.01); *H01M 4/136* (2013.01);
(Continued)

(58) Field of Classification Search
CPC ...... H01M 4/661; H01M 4/667; H01M 4/668; H01M 10/0525; H01M 4/133;
(Continued)

(56) References Cited

U.S. PATENT DOCUMENTS

2002/0037448 A1* 3/2002 Fitts .................... H01M 4/668
429/518
2003/0194605 A1* 10/2003 Fauteux ............ H01M 10/0486
429/149
(Continued)

FOREIGN PATENT DOCUMENTS

CN    1495942 A    5/2004
CN    1601801 A    3/2005
(Continued)

OTHER PUBLICATIONS

PCT International Search Report for PCT/CN2019/090407, dated Mar. 9, 2020, 11 pages.
(Continued)

*Primary Examiner* — Osei K Amponsah
(74) *Attorney, Agent, or Firm* — East IP P.C.

(57) ABSTRACT

This application discloses a lithium-ion secondary battery. The lithium-ion secondary battery includes a positive electrode plate, a negative electrode plate, a separator, and an electrolytic solution. The positive electrode plate includes a positive electrode current collector and a positive active material layer disposed on a surface of the positive electrode current collector and containing a positive active material, and the negative electrode plate includes a negative electrode current collector and a negative active material layer disposed on a surface of the negative electrode current collector and containing a negative active material; wherein the positive active material includes lithium iron phosphate, and the negative active material includes graphite; and wherein the positive electrode current collector and/or the
(Continued)

negative electrode current collector is a composite current collector, and the composite current collector includes an organic support layer and a conductive layer disposed on at least one surface of the organic support layer.

18 Claims, 2 Drawing Sheets

(51) Int. Cl.
| | |
|---|---|
| H01M 4/58 | (2010.01) |
| H01M 4/62 | (2006.01) |
| H01M 10/0525 | (2010.01) |
| H01M 10/0569 | (2010.01) |
| H01M 10/0567 | (2010.01) |
| H01M 4/133 | (2010.01) |
| H01M 4/136 | (2010.01) |
| C07C 317/12 | (2006.01) |
| H01M 4/02 | (2006.01) |

(52) U.S. Cl.
CPC ......... *H01M 4/587* (2013.01); *H01M 4/5825* (2013.01); *H01M 4/628* (2013.01); *H01M 10/0525* (2013.01); *H01M 10/0567* (2013.01); *H01M 10/0569* (2013.01); *H01M 2004/021* (2013.01); *H01M 2300/0037* (2013.01)

(58) Field of Classification Search
CPC ...... H01M 4/136; H01M 4/587; H01M 4/628; H01M 10/0567; H01M 10/0569; H01M 2300/0037
See application file for complete search history.

(56) References Cited

U.S. PATENT DOCUMENTS

| | | | |
|---|---|---|---|
| 2010/0112454 A1 | 5/2010 | Visco et al. | |
| 2015/0303521 A1 | 10/2015 | Sasaki et al. | |
| 2015/0318555 A1* | 11/2015 | Oku | B32B 27/365 429/245 |
| 2018/0301709 A1 | 10/2018 | Qiu | |
| 2021/0143440 A1 | 5/2021 | Liu et al. | |

FOREIGN PATENT DOCUMENTS

| | | |
|---|---|---|
| CN | 1906782 A | 1/2007 |
| CN | 101510625 A | 8/2009 |
| CN | 101803074 A | 8/2010 |
| CN | 101828293 A | 9/2010 |
| CN | 102037592 A | 4/2011 |
| CN | 104051784 A | 9/2014 |
| CN | 104157846 A | 11/2014 |
| CN | 104604003 A | 5/2015 |
| CN | 105742566 A | 7/2016 |
| CN | 105789611 A | 7/2016 |
| CN | 106298274 A | 1/2017 |
| CN | 106654285 A | 5/2017 |
| CN | 106785230 A | 5/2017 |
| CN | 107123812 A | 9/2017 |
| CN | 108258249 A | 7/2018 |
| CN | 108832134 A | 11/2018 |
| CN | 109119686 A | 1/2019 |
| CN | 109742436 A | 5/2019 |
| CN | 109786755 A | 5/2019 |
| EP | 3113273 A1 | 1/2017 |
| EP | 3447838 A1 | 2/2019 |
| EP | 3509145 A1 | 7/2019 |
| JP | H09213338 A | 8/1997 |
| JP | 1997283149 A | 10/1997 |
| JP | 1998112322 A | 4/1998 |
| JP | 1998112323 A | 4/1998 |
| JP | 1999102711 A | 4/1999 |
| JP | H1197030 A | 4/1999 |
| JP | 2001313037 A | 11/2001 |
| JP | 2002203562 A | 7/2002 |
| JP | 2004273132 A | 9/2004 |
| JP | 2009064767 A | 3/2009 |
| JP | 2009099480 A | 5/2009 |
| JP | 2010040488 A | 2/2010 |
| JP | 2010040489 A | 2/2010 |
| JP | 2010118258 A | 5/2010 |
| JP | 2012155974 A | 8/2012 |
| JP | 2013026041 A | 2/2013 |
| JP | 2014522549 A | 9/2014 |
| JP | 2016134241 A | 7/2016 |
| JP | 2017016879 A | 1/2017 |
| JP | 2018181451 A | 11/2018 |
| JP | 2018181796 A | 11/2018 |
| JP | 2018181823 A | 11/2018 |
| KR | 20040010259 A | 1/2004 |
| KR | 20170003393 A | 1/2017 |
| KR | 20180116096 A | 10/2018 |
| WO | 02/15302 A2 | 2/2002 |
| WO | WO2012127561 A1 | 9/2012 |
| WO | 2014034758 A1 | 3/2014 |
| WO | 2014080871 A1 | 5/2014 |
| WO | WO2017120594 A2 | 7/2017 |
| WO | WO2018062046 A1 | 4/2018 |
| WO | WO2018147137 A1 | 8/2018 |

OTHER PUBLICATIONS

Research Progress of Flexible Supercapacitors; Power Capacitor & Reactive Power Compensation; vol. 37, No. 5: 0078-0082 Oct. 2016.
Sang Woo Kim and Kuk Young Cho; Current Collectors for Flexible Lithium Ion Batteries: A Review of Materials; Journal of Electrochemical Science and Technology; J. Electrochem. Sci. Technol. 6(1), 10-15 (2015).
The First Office Action for Application Serial No. 201910473216.2; (PCT application in Chinese national phase) dated Aug. 26, 2020.
PRC Supplementary Search Report for Application No. 2019104732162, dated Nov. 5, 2020.
The extended European Search Report for European Application No. 19931444.4, dated Oct. 4, 2021, 9 pages.
The First Office Action for Japanese Application No. 2020-566300, dated Oct. 18, 2021, 8 pages.
The Second Office Action for European Application No. 19931444.4, dated May 30, 2022, 5 pages.
The First Office Action for European Application No. 19931444.4, dated Feb. 22, 2022, 4 pages.
The Decision of Rejection for Japanese Application No. 2020-566300, dated Mar. 7, 2022, 6 pages.
The First Office Action for Indian Application No. 202017054485, dated Jan. 5, 2022, 6 pages.
Metals, Metallic Elementsand Alloys-Thermal Conductivities, 11 pages.
The Intention to grant for European Application No. 19931444.4, dated Oct. 27, 2022, 8 pages.
The First Office Action for Korean Application No. 10-2020-7034296, dated Nov. 2, 2022, 17 pages.
The Second Office Action for Japanese Application No. 2019-190773, dated Oct. 18, 2022, 51 pages.
The First Office Action for Korean Application No. 10-2020-7034008, dated Nov. 2, 2022, 18 pages.
Nature of various substances: Nature of non-metallic solid, plastics, Internet archive., dated Oct. 18, 2022, 6 pages.
The First Office Action for Chinese Application No. 201910472635.4, dated Oct. 10, 2020, 21 pages.
The Second Office Action for Chinese Application No. 201910472635.4, dated Apr. 15, 2020, 25 pages.
The Extended European Search Report for European Application No. 20812892.6, dated Aug. 4, 2021, 8 pages.
The First Office Action for European Application No. 20812892.6, dated May 9, 2022, 5 pages.
The International Search Report for PCT Application No. PCT/CN2020/070449, dated Apr. 3, 2020, 19 pages.

(56) References Cited

OTHER PUBLICATIONS

The First Office Action for Indian Application No. 202017054339, dated Feb. 16, 2021, 6 pages.
The Reconsideration Report by Examiner before Appeal for Japanese Application No. 2019-190773, dated Jan. 19, 2022, 6 pages.
The First Office Action for Japanese Application No. 2019-190773, dated Dec. 1, 2020, 7 pages.
The Decision of Refusal for Japanese Application No. 2019-190773, dated Jul. 20, 2021, 6 pages.
The Notice-of-Allowance for U.S. Appl. No. 17/128,090, dated Jan. 31, 2023, 19 pages.

\* cited by examiner

LITHIUM-ION SECONDARY BATTERY

CROSS-REFERENCE TO RELATED APPLICATION

This application is a continuation of International Application No. PCT/CN2019/090407, filed on Jun. 6, 2019, which claims priority to Chinese Patent Application No. 201910473216.2 filed on May 31, 2019, both of which are incorporated herein by reference in their entireties.

TECHNICAL FIELD

This application belongs the field of an electrochemical device, and more particularly, this application relates to a lithium-ion secondary battery.

BACKGROUND

Lithium-ion secondary batteries have high charge and discharge performance, no memory effect, and are environmentally friendly. They are widely used in electric vehicles and consumer electronic products. Lithium iron phosphate is currently one of the most commonly used positive active materials for power batteries due to its high cycle life, good safety, and high temperature resistance. However, lithium-ion secondary batteries using lithium iron phosphate generally face the problem of poor low-temperature performance, and cannot meet the application requirements of the battery in a low-temperature environment.

SUMMARY

The embodiments of the present application provide a lithium-ion secondary battery, which aims to improve the low-temperature performance of the lithium-ion secondary battery using lithium iron phosphate.

The embodiments of the present application provide a lithium-ion secondary battery including a positive electrode plate, a negative electrode plate, a separator, and an electrolytic solution. The positive electrode plate includes a positive electrode current collector and a positive active material layer disposed on a surface of the positive electrode current collector and containing a positive active material; the negative electrode plate includes a negative electrode current collector and a negative active material layer disposed on a surface of the negative electrode current collector and containing a negative active material; wherein the positive active material includes lithium iron phosphate, and the negative active material includes graphite; and wherein the positive electrode current collector and/or the negative electrode current collector are composite current collector, and the composite current collector includes an organic support layer and a conductive layer disposed on at least one surface of the organic support layer.

In the lithium-ion secondary battery provided in the embodiments of the present application, the positive active material includes lithium iron phosphate, and the negative active material includes graphite, and the positive electrode current collector and/or the negative electrode current collector are composite current collector, and the composite current collector includes an organic support layer and a conductive layer disposed on at least one surface of the organic support layer. Since the organic support layer of the composite current collector is made of organic materials, compared with the conventional metal current collector, the composite current collector of the present application has a lower thermal conductivity and better thermal insulation performance. Thus when the battery is working in a low-temperature environment, it is less affected by the ambient temperature, and the heat generated by the battery itself will not quickly dissipate, which is conducive to ensuring that when the lithium-ion secondary battery is in a low-temperature environment, it still keeps a suitable working temperature inside the battery core. Thus, the problems of the poor kinetic performance of the lithium iron phosphate battery at low temperature are alleviated, so that the lithium iron phosphate battery has good low-temperature electrochemical performance and safety performance. In addition, the composite current collector has a smaller weight than conventional metal current collectors, so the weight energy density of the battery can be increased at the same time.

DESCRIPTION OF THE DRAWINGS

In order to explain the technical solutions of the embodiments of the present application more clearly, the following will briefly introduce the drawings that need to be used in the embodiments of the present application. Obviously, the drawings described below are only some embodiments of the present application. A person of ordinary skill in the art can obtain other drawings based on the drawings without creative work.

LABEL DESCRIPTION

Figure 1:
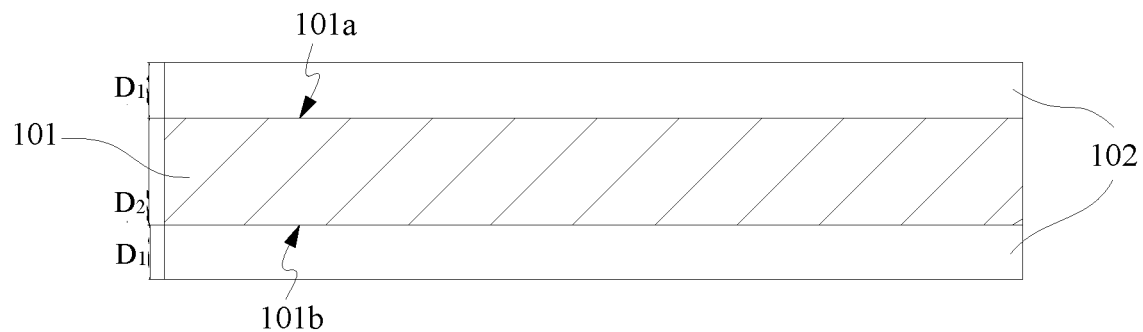
FIG. 1 is a schematic structural diagram of a composite current collector according to an embodiment of the present application.

10: a composite current collector;
101: an organic support layer;
101a: a first surface; 101b: a second surface;
1011: a first sub-layer; 1012: a second sub-layer; 1013: a third sub-layer;
102: a conductive layer;
103. a protective layer.

DETAILED DESCRIPTION

In order to make the purpose, technical solutions, and beneficial technical effects of the present application clearer, the present application will be further described in detail below in conjunction with embodiments. It should be understood that the embodiments described in this specification are only for explaining the application, not intending for limiting the application.

For the sake of brevity, only certain numerical ranges are explicitly disclosed herein. However, any lower limit may be combined with any upper limit to form a range that is not explicitly described; and any lower limit may be combined with other lower limits to form an unspecified range, and any upper limit may be combined with any other upper limit to form an unspecified range. Further, although not explicitly specified, each point or single value between the endpoints of the range is included in the range. Thus, each point or single value can be combined with any other point or single value or combined with other lower or upper limits to form a range that is not explicitly disclosed.

In the description herein, it should be noted that, unless otherwise stated, the recitation of numerical ranges by "above" and "below" include all numbers within that range including the endpoints. As used herein, "a", "an", "the", "at least one", and "one or more" are used interchangeably, unless indicated otherwise and the recitation of "more" in the phrase "one or more" includes two or more.

The above summary of the present application is not intended to describe each disclosed embodiment or every implementation in this application. The following description illustrates exemplary embodiments more specifically. In many places throughout the application, guidance is provided through a series of examples, which can be used in various combinations. In each instance, the enumeration is only a representative group and should not be interpreted as exhaustive.

The embodiments of the present application provide a lithium-ion secondary battery comprising a battery core and an electrolytic solution, wherein the battery core and the electrolytic solution may be packaged in a packaging case.

The battery core comprises a positive electrode plate, a separator and a negative electrode plate. The battery core can be formed by stacking or winding the positive electrode plate, the negative electrode plate, and the separator together. The separator is an insulator between the positive electrode plate and the negative electrode plate and can function as an isolation.

The positive electrode plate comprises a positive current collector and a positive active material layer disposed on the positive current collector, and the positive active material layer comprises a positive active material. The negative electrode plate comprises a negative current collector and a negative active material layer disposed on the negative current collector, and the negative active material layer comprises a negative active material. Through the intercalation and extraction of lithium ions between the positive active material and the negative active material, the charging and discharging of the lithium-ion secondary battery are realized.

The positive active material comprises lithium iron phosphate, and the negative active material comprises graphite, and the positive electrode current collector and/or the negative electrode current collector are the composite current collector 10.

FIG. 1 is a schematic structural diagram of a composite current collector 10 according to an embodiment of the present application. Please refer to FIG. 1. The composite current collector 10 comprises an organic support layer 101 and a conductive layer 102 that are stacked.

As shown in FIG. 1, the organic support layer 101 has a first surface 101a and a second surface 101b opposite in the thickness direction, and the conductive layer 102 is disposed on the first surface 101a and the second surface 101b of the organic support layer 101.

It can be understood that the conductive layer 102 may also be disposed on any one of the first surface 101a and the second surface 101b of the organic support layer 101. For example, the conductive layer 102 is disposed on the first surface 101a of the organic support layer 101. Of course, the conductive layer 102 may also be disposed on the second surface 101b of the organic support layer 101.

In the lithium-ion secondary battery of the embodiments of the present application, the positive active material comprises lithium iron phosphate, and the negative active material comprises graphite, and the positive electrode current collector and/or the negative electrode current collector are the composite current collector 10 which comprises the organic support layer 101 and the conductive layer 102 disposed on at least one surface of the organic support layer 101. Since the organic support layer 101 of the composite current collector 10 is made of organic materials, the thermal conductivity of the composite current collector 10 is smaller than that of the conventional metal current collector. The composite current collector 10 has better heat insulation/heat preservation performance, so when the battery is working in a low-temperature environment, it is less affected by the ambient temperature, and the heat generated by the battery itself will not quickly dissipate, which is conducive to ensuring that in the low-temperature environment the lithium-ion secondary battery can also maintain a suitable working temperature inside the battery core, thereby alleviating the disadvantage of the poor kinetic performance of the lithium iron phosphate battery at low temperature, making the lithium iron phosphate battery have good low-temperature electrochemical performance and safety performance.

In addition, the organic support layer 101 in the composite current collector 10 can also effectively support the conductive layer 102 and ensure the overall strength of the composite current collector 10. Therefore, compared with conventional metal current collectors, such as aluminum foil and copper foil, the thickness of the conductive layer 102 can be significantly reduced, and it is not easy to break.

Compared with conventional metal current collectors, since the thickness of the conductive layer 102 is significantly reduced, and the density of the organic support layer 101 is lower than that of metal, this ensures that the conductive layer 102 has good conductivity and current collecting performance. It is beneficial to reduce the weight of the battery cell and the lithium-ion secondary battery, thereby increasing the energy density of the lithium-ion secondary battery.

In addition, since both lithium iron phosphate and graphite have the characteristics of high cycle life, good safety, high temperature resistance, etc., it can make the battery core and the lithium-ion secondary battery using the battery core have high cycle performance, safety performance and good low-temperature performance and high-temperature performance.

In the composite current collector 10 of the embodiments of the present application, the thickness $D_1$ of the conductive layer 102 is preferably 30 nm≤D1≤3 μm. The thickness $D_1$ of the conductive layer 102 is within the above range, so that the conductive layer 102 has high conductivity and current collecting performance, which is beneficial to making the lithium-ion secondary battery have low impedance and reducing the battery polarization, thus improving the electrochemical performance of the lithium-ion secondary battery, among which the lithium-ion secondary battery has higher rate performance and cycle performance. The thickness $D_1$ of the conductive layer 102 is within the above range, which also makes the conductive layer 102 difficult to break during processing and use, so that the composite current collector 10 has higher mechanical stability and working stability, which is beneficial to improving the service life of the battery core and the lithium-ion secondary battery.

The thickness $D_1$ of the conductive layer 102 is 3 μm or less. In the case of abnormalities such as punctures in the lithium-ion secondary battery, the conductive layer 102 generates less burrs, which can reduce the risk of metal burrs contacting the counter electrode, thereby improving safety performance of the lithium-ion secondary battery.

In addition, arranging the conductive layer 102 with a smaller thickness on the surface of the organic support layer 101 can significantly reduce the weight of the composite current collector 10, thereby helping to reduce the weight of the lithium-ion secondary battery and to significantly improve the energy density of the lithium-ion secondary battery.

In some optional embodiments, the upper limit of the thickness $D_1$ of the conductive layer 102 can be selected from 3 µm, 2.5 µm, 2 µm, 1.8 µm, 1.5 µm, 1.2 µm, 1 µm, 900 nm, 750 nm, 450 nm, 250 nm, and 100 nm, and the lower limit can be selected from 1.6 µm, 1 µm, 800 nm, 600 nm, 400 nm, 300 nm, 150 nm, 100 nm, 80 nm, and 30 nm. The range of the thickness $D_1$ of the conductive layer 102 can be formed by a combination of any upper limit and any lower limit mentioned above, or it can be formed by combining any of the foregoing upper limit with any other upper limit, and may also be formed by combining any of the foregoing lower limit values and any other lower limit values.

Further preferably, the thickness $D_1$ of the conductive layer 102 is 300 nm≤D1≤2 µm. More preferably, the thickness $D_1$ of the conductive layer 102 is 500 nm≤D1≤1.5 µm. More preferably, the thickness $D_1$ of the conductive layer 102 is 800 nm≤D1≤1.2 µm.

The aforementioned "thickness $D_1$ of the conductive layer 102" refers to the thickness of the conductive layer 102 on one side of the organic supporting layer 101.

In the composite current collector 10 of the embodiments of the present application, the conductive layer 102 may comprise one or more of metal material, carbon-based conductive material, and conductive polymer material.

As the above-mentioned metal material, for example, it may comprise one or more of aluminum, aluminum alloy, copper, copper alloy, nickel, nickel alloy, iron, iron alloy, titanium, titanium alloy, silver and silver alloy, and for example, it may comprise one or more of aluminum, copper, nickel, iron, titanium, silver, nickel-copper alloy and aluminum-zirconium alloy.

As the above-mentioned carbon-based conductive material, for example, it may comprise one or more of graphite, superconducting carbon, acetylene black, carbon black, Ketjen black, carbon dots, carbon nanotubes, graphene, and carbon nanofibers.

As the above-mentioned conductive polymer material, for example, it may comprise one or more of polysulfur nitrides, aliphatic conjugated polymers, aromatic ring conjugated polymers, and aromatic heterocyclic conjugated polymers. As an example, the conductive polymer material may comprise one or more of polyacetylene, polyphenylene, polypyrrole, polyacetylene, polyaniline, polythiophene, and polypyridine. In addition, the electron delocalization of the conductive polymer material can be increased by doping and thus the conductivity can be improved.

In some embodiments, when the composite current collector 10 is used as a positive electrode current collector, the conductive layer 102 preferably comprise aluminum or an aluminum alloy, wherein the weight percentage of aluminum element in the aluminum alloy is preferably 80 wt % or more, more preferably 90 wt % the above. When the composite current collector 10 is used as a negative electrode current collector, the conductive layer 102 preferably comprises copper or a copper alloy, wherein the weight percentage of the copper element in the copper alloy is preferably 80 wt % or more, more preferably 90 wt % or more.

In the composite current collector 10 of the embodiments of the present application, the volume resistivity of the conductive layer 102 is preferably less than or equal to $8.0 \times 10^{-8}$ Ω·m. This is beneficial for the conductive layer 102 to have better conductivity and current collection performance, thereby improving the rate performance and cycle performance of the lithium-ion secondary battery.

Further, when the composite current collector 10 is used as a positive electrode current collector, the volume resistivity of the conductive layer 102 is preferably $3.2 \times 10^{-8}$ Ω·m $7.8 \times 10^{-8}$ Ω·m; when the composite current collector 10 is used as a negative electrode current collector, the volume resistivity of the conductive layer 102 is preferably $1.65 \times 10^{-8}$ Ω·m to $3.3 \times 10^{-8}$ Ω·m. This is conducive to making the conductive layer 102 have better electrical conductivity and current collection performance, while also enabling the lithium-ion secondary battery to further have low impedance and to reduce the polarization of the negative electrode, so that the lithium-ion secondary battery has high rate performance and cycle performance, especially under low-temperature conditions, better improving the kinetic performance of lithium-ion secondary batteries, and ensuring good low-temperature electrochemical performance such as low-temperature rate performance.

In the composite current collector 10 of the embodiments of the present application, the thickness $D_2$ of the organic support layer 101 is preferably 1 µm≤D2≤30 µm. If the thickness $D_2$ of the organic support layer 101 is within the above range, the organic support layer 101 can better perform the function of heat preservation and thermal storage for the battery core and the lithium-ion secondary battery, and improve the low-temperature performance of the lithium-ion secondary battery; it can also ensure that the organic support layer 101 has high mechanical strength, is not easy to break during processing and use, provides good support and protection to the conductive layer 102, and improves the mechanical stability and working stability of the composite current collector 10.

The thickness $D_2$ of the organic support layer 101 is 30 µm or less, which is beneficial to making the lithium-ion secondary battery have a smaller volume and a lower weight, thereby increasing the volume energy density and weight energy density of the lithium-ion secondary battery.

In some optional embodiments, the upper limit of the thickness $D_2$ of the organic support layer 101 can be selected from 30 µm, 25 µm, 20 µm, 18 µm, 15 µm, 12 µm, 10 µm, and 8 µm, and the lower limit can be selected from 1 µm, 1.5 µm, 2 µm, 3 µm, 4 µm, 5 µm, 6 µm, 7 µm, 9 µm, and 16 µm. The range of the thickness $D_2$ of the organic support layer 101 can be formed by a combination of any upper limit with any lower limit as mentioned above, or can be formed by a combination of any upper limit with any other upper limit as mentioned above, or can be formed by any combination of any lower limit with any other lower limit as mentioned above.

Further preferably, the thickness $D_2$ of the organic support layer 101 is 1 nm≤D1≤20 µm. More preferably, the thickness $D_2$ of the organic support layer 101 is 1 µm≤D2≤15 µm. More preferably, the thickness $D_2$ of the organic support layer 101 is 1 µm≤D2≤10 µm. More preferably, the thickness $D_2$ of the organic support layer 101 is 1 µm≤D2≤8 µm, preferably 2 µm≤D2≤8 µm.

In the composite current collector 10 of the embodiments of the present application, the Young's modulus E of the organic support layer 101 is preferably E 2 GPa, which makes the organic support layer 101 rigid, not only satisfying the higher support effect of the organic support layer 101 on the conductive layer 102, to ensure the overall strength of the composite current collector 10, but also preventing the organic support layer 101 from being excessively stretched or deformed during the processing of the composite current collector 10, and more effectively preventing the organic support layer 101 and the conductive layer 102 from breaking. At the same time, the bonding strength between the organic support layer 101 and the conductive layer 102 is higher, so that the conductive layer 102 is not easily peeled off, and the mechanical stability and working stability of the composite current collector 10 are improved, thereby further improving the performances of the lithium-ion secondary battery.

Further, the Young's modulus E of the organic support layer 101 is preferably 2 GPa≤E≤20 GPa; for example, 2 GPa, 3 GPa, 4 GPa, SGPa, 6 GPa, 7 GPa, 8 GPa, 9 GPa, 10 GPa, 11 GPa, 12 GPa, 13 GPa, 14 GPa, 15 GPa, 16 GPa, 17 GPa, 18 GPa, 19 GPa, and 20 GPa. This allows the organic support layer 101 to have rigidity and suitable toughness at the same time, so as to ensure the flexibility of the organic support layer 101 and the composite current collector 10 using it for winding during processing.

In the composite current collector 10 of the embodiments of the present application, the organic support layer 101 adopts one or more of polymer materials and polymer-based composite materials.

As the above-mentioned polymer material, for example, it may be one or more of polyamides, polyimides, polyesters, polyolefins, polyalkynes, siloxane polymers, polyethers, polyols, polysulfones, polysaccharide polymers, amino acid polymers, polysulfur nitrides, aromatic ring polymers, aromatic heterocyclic polymers, epoxy resins, phenolic resins, the derivatives thereof, the cross-linked products thereof and the copolymers thereof.

Further, the polymer material may be, for example, one or more of polycaprolactam (commonly known as nylon 6), polyhexamethylene adipamide (commonly known as nylon 66), polyparaphenylene terephthalamide (PPTA), polyisophthalamide M-phenylenediamine (PMIA), polyethylene terephthalate (PET), polybutylene terephthalate (PBT), polyethylene naphthalate (PEN), polycarbonate (PC), polyethylene (PE), polypropylene (PP), poly(propylene-ethylene) (PPE), polyvinyl alcohol (PVA), polystyrene (PS), polyvinyl chloride (PVC), polyvinylidene fluoride (PVDF), polytetrafluoroethylene (PTEE), polystyrene sulfonate (PSS), polyacetylene (PA), silicone rubber, polyoxymethylene (POM), polyphenylene oxide (PPO), polyphenylene sulfide (PPS), polyethylene glycol (PEG), cellulose, starch, protein, polyphenylene, polypyrrole (PPy), polyaniline (PAN), polythiophene (PT), polypyridine (PPY), acrylonitrile-butadiene-styrene copolymers (ABS), the derivatives thereof, the cross-linked products thereof, and the copolymers thereof.

As the above-mentioned polymer-based composite material, for example, it may include the above-mentioned polymer material and an additive, and the additive may be one or more of metal materials and inorganic non-metal materials.

The aforementioned metal material additive is, for example, one or more of aluminum, aluminum alloy, copper, copper alloy, nickel, nickel alloy, titanium, titanium alloy, iron, iron alloy, silver, and silver alloy.

The above-mentioned inorganic non-metal material additive is, for example, one or more of carbon-based materials, alumina, silicon dioxide, silicon nitride, silicon carbide, boron nitride, silicate, and titanium oxide, and for example, one or more of glass materials, ceramic materials and ceramic composite materials. The carbon-based material additive is, for example, one or more of graphite, superconducting carbon, acetylene black, carbon black, Ketjen black, carbon dots, carbon nanotubes, graphene, and carbon nanofibers.

As the above additive, it may also be a carbon-based material coated with a metal material, such as one or more of nickel-coated graphite powder and nickel-coated carbon fiber.

Preferably, the organic support layer 101 adopts one or more of insulating polymer materials and insulating polymer-based composite materials. The organic support layer 101 has a relatively high volume resistivity, which is beneficial to improving the safety performance of the lithium-ion secondary battery.

Further, the organic support layer 101 comprises one or more of polyethylene terephthalate (PET), polybutylene terephthalate (PBT), polyethylene naphthalate (PEN), sodium polystyrene sulfonate (PSS Na) and polyimide (PI).

In the composite current collector 10 of the embodiments of the present application, the organic support layer 101 may be a single-layer structure or a composite layer structure of more than two layers, such as two layers, three layers, and four layers.

Figure 2:
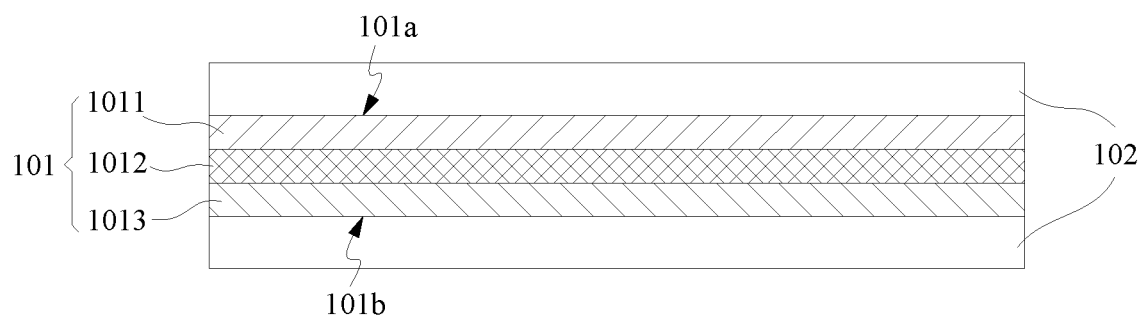
FIG. 2 is a schematic structural diagram of a composite current collector according to another embodiment of the present application.

FIG. 2 is a schematic structural diagram of another composite current collector 10 according to an embodiment of the present application. Please refer to FIG. 2. The organic support layer 101 is a composite layer structure formed from the stacking of a first sub-layer 1011, a second sub-layer 1012, and a third sub-layer 1013. The organic support layer 101 of the composite layer structure has a first surface 101a and a second surface 101b opposite to each other, and the conductive layer 102 is stacked on the first surface 101a and the second surface 101b of the organic support layer 101. Of course, the conductive layer 102 may be disposed only on the first surface 101a of the organic support layer 101, or only on the second surface 101b of the organic support layer 101.

When the organic support layer 101 has a composite layer structure of more than two layers, the materials of each sub-layer may be the same or different.

The thermal conductivity of the composite current collector 10 is preferably 0.01 W/(m·K) to 10 W/(m·K). If the thermal conductivity of the composite current collector 10 is higher than 10 W/(m·K), it is not enough to improve the low-temperature electrochemical performance and low-temperature lithium precipitation of the entire battery; if the thermal conductivity of the composite current collector 10 is less than 0.01 W/(m·K), the thickness of the organic support layer 101 is generally larger, which will affect the volume energy density and weight energy density of the battery.

More preferably, the thermal conductivity of the composite current collector 10 is 0.1 W/(m·K) 2 W/(m·K).

The thermal conductivity of the composite current collector 10 will be affected by the following factors: the thickness $D_1$ of the conductive layer 102, the material of the conductive layer 102, the thickness $D_2$ of the organic support layer 101, the material of the organic support layer 101, and the preparation process conditions of the conductive layer 102 (for example, the deposition rate, deposition temperature and cooling rate when the conductive layer 102 is prepared by a deposition process), the bonding force between the conductive layer 102 and the organic support layer 101, and the like. By adjusting one or more of the aforementioned factors, the thermal conductivity of the composite current collector 10 can be improved.

Figure 3:
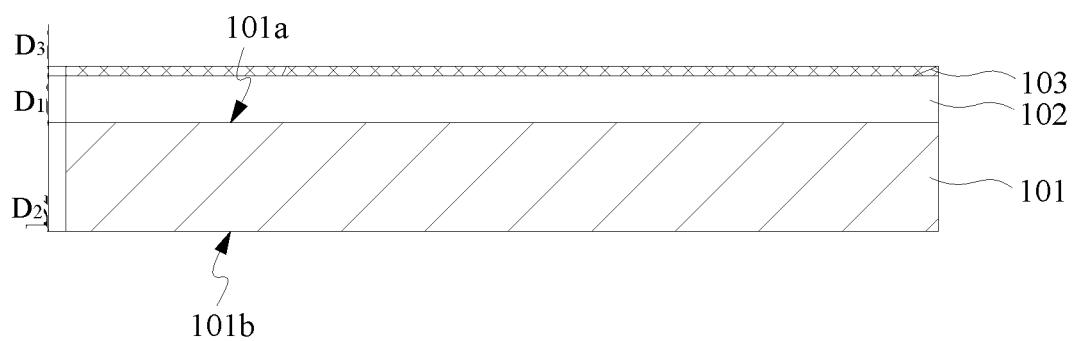
FIG. 3 is a schematic structural diagram of a composite current collector according to another embodiment of the present application.
Figure 4:
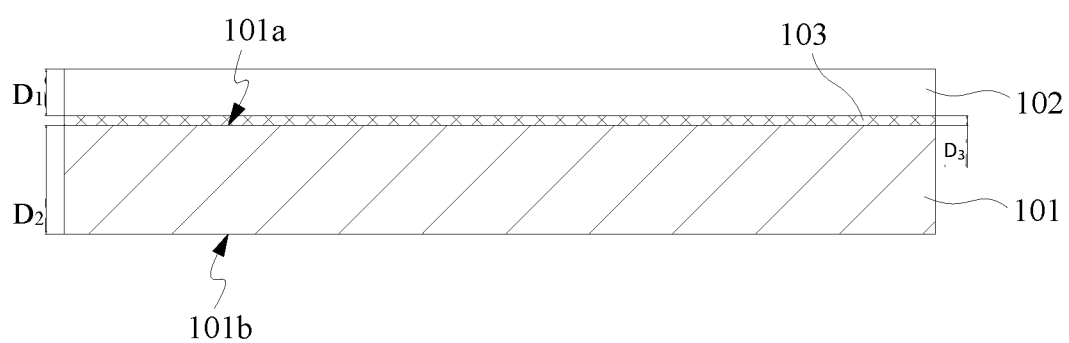
FIG. 4 is a schematic structural diagram of a composite current collector according to another embodiment of the present application.
Figure 5:
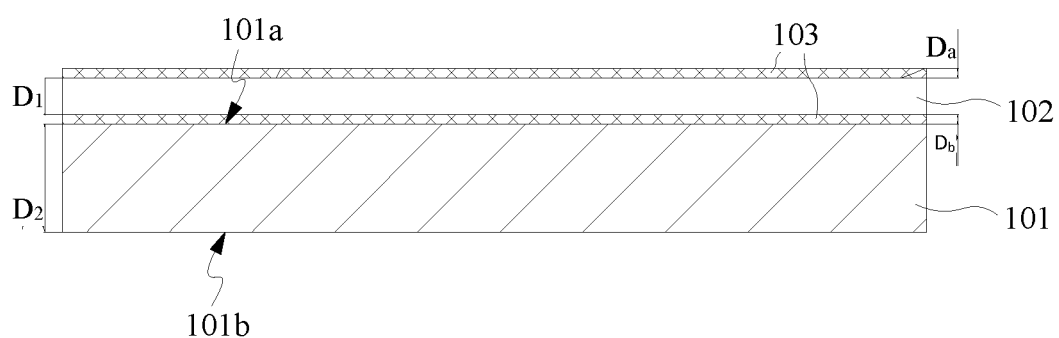
FIG. 5 is a schematic structural diagram of a composite current collector according to another embodiment of the present application.

The composite current collector 10 of the embodiments of the present application further optionally comprises a protective layer 103. Referring to FIGS. 3 to 5, the conductive layer 102 comprises two opposite surfaces in its thickness direction, and the protective layer 103 is stacked on either or both of the two surfaces of the conductive layer 102 to protect the conductive layer 102, to prevent damages such as chemical corrosion or mechanical damage to the conductive layer 102, and to ensure the working stability and service life of the composite current collector 10, so that the lithium-ion secondary battery has higher safety performance and electrochemical performance. In addition, the protective layer 103 can also enhance the strength of the composite current collector 10.

It is understandable that although FIGS. 3 to 5 show that there is a conductive layer 102 on one side of the organic support layer 101, a protective layer 103 on one or both of the two opposite surfaces in the thickness direction of the conductive layer 102, in other embodiments, it is also possible to have conductive layers 102 on the two opposite surfaces of the organic support layer 101, respectively, to have a protective layer 103 on one or both of the two opposite surfaces in the thickness direction of either conductive layer 102, or to have a protective layer 103 on one or both of the two opposite surfaces in the thickness direction of the both conductive layers 102.

The protective layer 103 comprises one or more of metal, metal oxide, and conductive carbon. Among them, the protective layer 103 of metal material is a metal protective layer, and the protective layer 103 of metal oxide material is a metal oxide protective layer.

The aforementioned metal is, for example, one or more of nickel, chromium, nickel-based alloy, and copper-based alloy. The aforementioned nickel-based alloy is an alloy formed by adding one or more other elements to pure nickel as a matrix, preferably a nickel-chromium alloy. Nickel-chromium alloy is an alloy formed by metallic nickel and metallic chromium. Optionally, the weight ratio of nickel to chromium in the nickel-chromium alloy is from 1:99 to 99:1, such as 9:1. The aforementioned copper-based alloy is an alloy formed by adding one or more other elements to pure copper as a matrix, preferably a nickel-copper alloy. Optionally, the weight ratio of nickel to copper in the nickel-copper alloy is from 1:99 to 99:1, such as 9:1.

The aforementioned metal oxide is, for example, one or more of alumina, cobalt oxide, chromium oxide, and nickel oxide.

The aforementioned conductive carbon is, for example, one or more of graphite, superconducting carbon, acetylene black, carbon black, Ketjen black, carbon dots, carbon nanotubes, graphene, and carbon nanofibers, and further is one or more of carbon black, carbon nanotubes, acetylene black and graphene.

As some examples, referring to FIG. 3, the composite current collector 10 includes an organic support layer 101, a conductive layer 102 and a protective layer 103 that are stacked, wherein the organic support layer 101 has a first surface 101a and a second surface 101b opposite to each other in the thickness direction, and the conductive layer 102 is stacked on at least one of the first surface 101a and the second surface 101b of the organic support layer 101, and the protective layer 103 is stacked on the surface of the conductive layer 102 facing away from the organic support layer 101.

A protective layer 103 (referred to as the upper protective layer for short) is disposed on the surface of the conductive layer 102 facing away from the organic support layer 101 to protect the conductive layer 102 from chemical corrosion and mechanical damage, and can also improve the interface of composite current collector 10 with the active material layer, so as to improve the bonding force between the composite current collector 10 and the active material layer.

In some embodiments, the upper protective layer of the composite current collector 10 is preferably at least one of a metal protective layer and a metal oxide protective layer. The metal oxide protective layer and the metal protective layer have high mechanical strength, high corrosion resistance and large specific surface area. Thus, the conductive layer 102 can be better prevented from chemical corrosion or mechanical damage, and at the same time, the interface bonding force between the conductive layer 102 and the positive active material layer can be improved, and the performance of the lithium-ion secondary battery can be improved.

Further, when the composite current collector 10 is used as a positive electrode current collector, the upper protective layer of the composite current collector 10 is preferably a metal oxide protective layer, such as aluminum oxide, cobalt oxide, nickel oxide, and chromium oxide. The metal oxide protective layer has high hardness and mechanical strength, a larger specific surface area, and better corrosion resistance, and can better protect the conductive layer 102; in addition, it is also beneficial to improving the nail penetration safety performance of the battery.

Or further, when the composite current collector 10 is used as a negative electrode current collector, the upper protective layer is preferably a metal protective layer. The metal protective layer can improve the conductivity of the composite current collector 10, reduce battery polarization, and reduce the lithium precipitation of the negative electrode. Risk, and improve the cycle performance and safety performance of lithium-ion secondary batteries. More preferably the upper protective layer is double protective layers, i.e., a composite layer of a metal protective layer and a metal oxide protective layer, wherein preferably, the metal protective layer is disposed on the surface of the conductive layer 102 facing away from the organic supporting layer 101, and the metal oxide protective layer is disposed on the surface of the metal protective layer facing away from the organic supporting layer 101. This can improve the conductivity, corrosion resistance, and the interface of the conductive layer 102 with the negative active material layer, etc., and it can obtain a negative electrode current collector with better comprehensive properties.

As other examples, referring to FIG. 4, the composite current collector 10 comprises an organic support layer 101, a conductive layer 102 and a protective layer 103 that are stacked, wherein the organic support layer 101 has a first surface 101a and a second surface 101b opposite to each other in the thickness direction, and the conductive layer 102 is stacked on at least one of the first surface 101a and the second surface 101b of the organic support layer 101, and the protective layer 103 is stacked on the surface of the conductive layer 102 facing to the organic support layer 101.

A protective layer 103 (referred to as a lower protective layer for short) is disposed on the surface of the conductive layer 102 facing to the organic support layer 101. The lower protective layer protects the conductive layer 102 from chemical corrosion and mechanical damage, and can also improve the bonding force between the conductive layer 102 and the organic support layer 101 to prevent the conductive layer 102 from being separated from the organic support layer 101, and can improve the support and protection effect to the conductive layer 102.

Optionally, the lower protective layer is a metal oxide protective layer or a metal protective layer. The metal protective layer and the metal oxide protective layer have high corrosion resistance and a large specific surface area, which can further improve the interface bonding force between the conductive layer 102 and the organic support layer 101, making the lower protective layer better protect the conductive layer 102 and improve the performance of the lithium-ion secondary battery. Among them, the metal oxide protective layer has higher hardness and better mechanical strength, which is more conducive to improving the strength of the composite current collector 10. When the composite current collector 10 is used as a positive electrode current collector, the lower protective layer is preferably a metal oxide protective layer. When the composite current collector 10 is used as a negative electrode current collector, the lower protective layer is preferably a metal protective layer, which can protect the conductive layer 102 from chemical corrosion and mechanical damage while also improving the conductivity performance of the composite current collector 10, can reduce battery polarization, reduce the risk of lithium precipitation in the negative electrode, and improve the cycle performance and safety performance of the lithium-ion secondary battery.

As still other examples, referring to FIG. 5, the composite current collector 10 comprises an organic support layer 101, a conductive layer 102, and a protective layer 103 that are stacked, wherein the organic support layer 101 has a first surface 101a and a second surface 101b opposite to each other in the thickness direction, and the conductive layer 102 is stacked on at least one of the first surface 101a and the second surface 101b of the organic support layer 101, and the protective layer 103 is stacked on the surface of the conductive layer 102 facing away from the organic supporting layer 101 and on the surface facing to the organic supporting layer 101.

The protective layer 103 is disposed on both surfaces of the conductive layer 102 to more fully protect the conductive layer 102, so that the composite current collector 10 has a higher comprehensive properties.

It can be understood that the materials of the protective layers 103 on the two surfaces of the conductive layer 102 may be the same or different, and the thickness may be the same or different.

Preferably, the thickness $D_3$ of the protective layer 103 is 1 nm≤$D_3$≤200 nm, and $D_3$≤0.1$D_1$. If the protective layer 103 is too thin, it will not be enough to protect the conductive layer 102; if it is too thick, the energy density of the lithium-ion secondary battery will be reduced.

In some embodiments, the upper limit of the thickness $D_3$ of the protective layer 103 may be 200 nm, 180 nm, 150 nm, 120 nm, 100 nm, 80 nm, 60 nm, 55 nm, 50 nm, 45 nm, 40 nm, 30 nm, or 20 nm, and the lower limit may be 1 nm, 2 nm, 5 nm, 8 nm, 10 nm, 12 nm, 15 nm, or 18 nm. The range of the thickness $D_3$ of the protective layer 103 can be formed by a combination of any upper limit with any lower limit as described above, or can be formed by a combination of any upper limit with any other upper limit as described above, or can be formed by any lower limit with any other lower limit as described above.

More preferably, the thickness $D_3$ of the protective layer 103 is 5 nm≤$D_3$≤200 nm, and more preferably 10 nm≤$D_3$≤200 nm.

The aforementioned "thickness $D_3$ of the protective layer 103" refers to the thickness of the protective layer 103 located on one side of the conductive layer 102. That is to say, the thickness $D_a$ of the upper protective layer is 1 nm≤$D_a$≤200 nm and $D_a$≤0.1$D_1$; further, 5 nm≤$D_a$≤200 nm; and further, 10 nm≤$D_a$≤200 nm. The thickness $D_b$ of the lower protective layer is 1 nm≤$D_b$≤200 nm, and $D_b$≤0.1$D_1$; further, 5 nm≤$D_b$≤200 nm; and further, 10 nm≤$D_b$≤200 nm.

When the protective layer 103 is disposed on both surfaces of the conductive layer 102, i.e., when the composite current collector 10 comprises an upper protective layer and a lower protective layer, preferably, $D_a$>$D_b$, which is beneficial for the upper protective layer and the lower protective layer to cooperate with each other to conduct electricity. The layer 102 has a good protective effect against chemical corrosion and mechanical damage, and at the same time enables the lithium-ion secondary battery to have a higher energy density. More preferably, 0.5≤$D_a$≤$D_b$≤0.8 $D_a$ can better exert the synergistic protective effect of the upper protective layer and the lower protective layer.

It can be understood that the influence of the setting of the protective layer 103 on the thermal conductivity of the composite current collector 10 is negligible.

In some embodiments, the bonding force F between the organic support layer 101 and the conductive layer 102 is preferably F≤100 N/m, more preferably F≤400 N/m. This can effectively prevent peeling between the organic support layer 101 and the conductive layer 102, and improve the overall strength and reliability, thereby helping to improve the performance of the lithium-ion secondary battery.

In the composite current collector 10 of the embodiments of the present application, when the conductive layer 102 is made of a metal material, it can be formed on the organic support layer 101 by at least one of mechanical rolling, bonding, vapor deposition, electroless plating, and electroplating method. Among them, vapor deposition and electroplating are preferred. The conductive layer 102 is formed on the organic support layer 101 by a vapor deposition method or an electroplating method, which is beneficial to making the bonding between the conductive layer 102 and the organic support layer 101 stronger.

The above-mentioned vapor deposition method is preferably a physical vapor deposition method. The physical vapor deposition method is preferably at least one of an evaporation method and a sputtering method, wherein the evaporation method is preferably at least one of a vacuum evaporation method, a thermal evaporation method, and an electron beam evaporation method, and wherein the sputtering method is preferably a magnetron sputtering method.

As an example, the conditions for forming the conductive layer 102 by mechanical rolling are as follows: a metal foil is placed in a mechanical roll, rolled to a predetermined thickness by applying a pressure of 20 t~40 t, and disposed on the surface of the organic support layer 101 after surface cleaning treatment, and then placed in a mechanical roller, and the metal foil and the surface of the organic support layer 101 are tightly combined by applying a pressure of 30 t to 50 t.

The conditions for forming the conductive layer 102 by bonding are as follows: a metal foil is placed in a mechanical roller, and rolled to a predetermined thickness by applying a pressure of 20 t to 40 t; then a surface the organic support layer 101 subjected to a surface cleaning treatment is coated with a mixed solution of polyvinylidene fluoride (PVDF) and N-methylpyrrolidone (NMP); finally, the conductive layer 102 with the predetermined thickness is bonded to the surface of the organic support layer 101, and dried to make the two tightly bonded.

The conditions for forming the conductive layer by the vacuum evaporation method are as follows: the organic support layer 101 subjected to a surface cleaning treatment is placed in the vacuum coating chamber; and the high-purity metal wire in the metal evaporation chamber is melted and evaporated at a high temperature of 1300° C.~2000° C.; and the evaporated metal passes through the cooling system in the vacuum coating chamber and is finally deposited on the surface of the organic support layer 101 to form the conductive layer 102.

When a carbon-based conductive material is used for the conductive layer 102, it may be formed on the organic support layer 101 by at least one of mechanical rolling, bonding, vapor deposition, in-situ formation, and coating method.

When the conductive layer 102 is made of a conductive polymer material, it may be formed on the organic support layer 101 by at least one of mechanical rolling, bonding, in-situ formation method, and coating method.

When the composite current collector 10 has a protective layer 103, the protective layer 103 may be formed on the conductive layer 102 by at least one of vapor deposition, in-situ formation, and coating method. The vapor deposition method may be the vapor deposition method as described above. The in-situ formation method is preferably an in-situ passivation method, i.e., a method of forming a metal oxide passivation layer in situ on the metal surface. The coating method is preferably at least one of roll coating, extrusion coating, knife coating, and gravure coating.

Preferably, the protective layer 103 is formed on the conductive layer 102 by at least one of a vapor deposition method and an in-situ formation method, which is beneficial to making the conductive layer 102 and the protective layer 103 have a higher bonding force, Thus the protective layer 102 better protects the composite current collector 10 and ensures the working performance of the composite current collector 10.

The composite current collector 10 of any of the foregoing embodiments can be used as either or both of the positive electrode current collector and the negative electrode current collector.

In some embodiments, the positive electrode current collector is a metal current collector (for example, an aluminum foil or aluminum alloy current collector) or a composite current collector 10, and the negative electrode current collector is a composite current collector 10. Due to the high density of copper, replacing the conventional copper-foil negative electrode current collector with the composite current collector 10 can greatly improve the weight energy density of the lithium-ion secondary battery and at the same time improve the low-temperature performance of the lithium-ion secondary battery. In addition, the use of composite current collector 10 at the negative electrode plate can improve the low-temperature performance of the lithium-ion secondary battery, and at the same time, better prevent the low-temperature lithium precipitation of the negative electrode, and better improve the kinetic performance, rate performance and safety performance of the lithium-ion secondary battery.

When both the positive electrode current collector and the negative electrode current collector are the composite current collector 10, the low-temperature performance of the lithium-ion secondary battery can be better improved.

In this context, the thickness $D_1$ of the conductive layer 102 and the thickness $D_2$ of the organic support layer 101 can be measured using instruments and methods known in the art, for example, a high accuracy micrometer.

The thermal conductivity of the composite current collector 10 can be measured using instruments and methods known in the art. For example, a thermal conductivity meter is used, including: cutting the composite current collector 10 into a 5 cm×5 cm sample, and measuring the sample with a TC3000 thermal conductivity meter to measure the thermal conductivity.

The volume resistivity p of the conductive layer 102 is $\rho=R_{s\times d}$, where the unit of $\rho$ is $\Omega \cdot m$; $R_s$ is the square resistance of the conductive layer 102 in $\Omega$; d is the thickness of the conductive layer 102 in m. The four-probe method is used to test the square resistance $R_s$ of the conductive layer 102. The method includes: using the RTS-9 double-electric four-probe tester, wherein the test environment is: normal temperature 23±2° C., 0.1 MPa, relative humidity ≤65%. During the test, the surface of the positive electrode collector 10 sample is cleaned, and placed horizontally on the test bench, and then the four probes are put down. Make the probes contact with the surface of the conductive layer 102 of the sample, and then adjust the automatic test mode to calibrate the current range of the sample, and carry out the square resistance measurement under the appropriate current range, and collect 8 to 10 data points of the same sample for the data measurement accuracy and error analysis. Finally, the average value is taken and recorded as the square resistance of the conductive layer 102.

The Young's modulus E of the organic support layer 101 can be measured by a method known in the art. As an example, cut the organic support layer 101 into a 15 mm×200 mm sample, measure the thickness h (μm) of the sample with a micrometer, and perform a tensile test using Gotech tensile machine at room temperature and normal pressure (25° C., 0.1 MPa). Set the initial position so that the sample between the clamps is 50 mm long and the tensile speed is 5 mm/min. Record the tensile load L(N) and the equipment displacement y(mm) until the sample breaks, then calculate the stress ε(GPa)=L/(15×h), strain η=y/50, and draw a stress-strain curve, and take the initial linear region of the curve, the slope of the curve is the Young's modulus E.

The bonding force F between the organic support layer 101 and the conductive layer 102 can be tested by methods known in the art. For example, the composite current collector 10 sample with the conductive layer 102 disposed on one side of the organic support layer 101 is selected to be tested, and the width d is 0.02 m. Under normal temperature and pressure (25° C., 0.1 MPa), use 3M double-sided tape to evenly paste on the stainless steel plate, then evenly paste the sample to be tested on the double-sided tape, and use a Gotech tensile machine to peel the conductive layer 102 from the organic support layer 101, and the maximum tensile force x(N) is read according to the data graph of tensile force and displacement, and the bonding force F between the conductive layer 102 and the organic support layer 101 is calculated according to F=x/d (N/m).

Positive Electrode Plate

An embodiment of the present application provides a positive electrode plate for a lithium-ion secondary battery. The positive electrode plate comprises a positive current collector and a positive active material layer disposed on the positive current collector. As an example, the positive electrode current collector comprises two opposite surfaces in its thickness direction, and the positive active material layer is stacked on the two surfaces of the positive electrode current collector. Of course, the positive active material layer can also be stacked on any one of the two surfaces of the positive electrode current collector.

If the negative electrode current collector is a metal current collector, the positive electrode current collector is the aforementioned composite current collector 10. If the negative electrode current collector is the aforementioned composite current collector 10, the positive electrode current collector can be the aforementioned composite current collector 10, or it can be a metal current collector, such as aluminum foil or aluminum alloy.

When the positive electrode current collector is the composite current collector 10 as described above, it not only has the corresponding beneficial effects described above, but also can improve the safety performance of the lithium-ion secondary battery.

The positive active material layer comprises a positive active material, and the positive active material comprises lithium iron phosphate.

The positive active material layer may optionally comprise other positive active materials known in the art that can perform reversible intercalation/deintercalation of lithium ions.

Other positive active materials can be, for example, one or more of lithium cobalt oxide, lithium nickel oxide, lithium manganese oxide, lithium nickel manganese oxide, lithium nickel cobalt manganese oxide, lithium nickel cobalt aluminum oxide, lithium vanadium phosphate, lithium cobalt phosphate, lithium manganese phosphate, lithium iron manganese phosphate, lithium iron silicate, lithium vanadium silicate, lithium cobalt silicate, lithium manganese silicate, and lithium titanate. For example, other positive active materials are one or more of $LiMn_2O_4$, $LiNiO_2$, $LiCoO_2$, $LiNi_{1-y}Co_yO_2$ (0<y<1), $LiNi_aCo_bAl_{1-a-b}O_2$ (0<a<1, 0<b<1, 0<a+b<1), $LiMn_{1-m-n}Ni_mCo_nO_2$ (0<m<1, 0<n<1, 0<m+n<1), $LiMPO_4$ (M can be one or more of Mn, Co and Fe) and $Li_3V_2(PO_4)_3$.

Optionally, the mass percentage of lithium iron phosphate in the positive e active material is more than 50 wt %, further more than 60 wt %, and still further more than 80 wt %. At this time, the low-temperature performance of the lithium-ion secondary battery in the embodiments of the present application can be more significantly improved.

The positive active material layer may also optionally include a binder, and the type of the binder is not limited in this application. As an example, the binder is one or more of styrene butadiene rubber (SBR), water-based acrylic resin, carboxymethyl cellulose (CMC), polyvinylidene fluoride (PVDF), polytetrafluoroethylene (PTFE), ethylene-vinyl acetate copolymer (EVA), polyvinyl alcohol (PVA) and polyvinyl butyral (PVB).

The positive active material layer may also optionally comprise a conductive agent, and the type of the conductive agent is not limited in this application. As an example, the conductive agent is one or more of graphite, superconducting carbon, acetylene black, carbon black, Ketjen black, carbon dots, carbon nanotubes, graphene, and carbon nanofibers.

The thickness $T_1$ of the positive active material layer is preferably from 50 μm to 100 μm. If the thickness $T_1$ of the positive active material layer is within the above range, the effect of improving the low-temperature performance of the lithium-ion secondary battery is better, and at the same time, it can ensure that the positive electrode has good kinetic performance and can improve the electrochemical performance of the lithium-ion secondary battery. More preferably, the thickness $T_1$ of the positive active material layer is from 60 μm to 90 μm, which can further improve the low-temperature performance of the lithium-ion secondary battery, and obtain a positive electrode plate and a lithium-ion secondary battery with better comprehensive properties.

The aforementioned "thickness $T_1$ of the positive active material layer" refers to the thickness of the positive active material layer on one side of the positive electrode current collector.

The positive electrode plate can be prepared according to a conventional method in the art, such as a coating method. As an example, the positive active material and the optional conductive agent and binder are dispersed in a solvent which can be N-methylpyrrolidone (NMP) to form a uniform positive electrode slurry; the positive electrode slurry is coated on the positive electrode current collector; after drying and other processes, a positive electrode plate is obtained.

Negative Electrode Plate

An embodiment of the present application provide a negative electrode plate for a lithium-ion secondary battery. The negative electrode plate comprises a negative current collector and a negative active material layer disposed on the negative current collector. As an example, the negative electrode current collector comprises two opposite surfaces in its thickness direction, and the negative active material layer is stacked on the two surfaces of the negative electrode current collector. Of course, the negative active material layer may also be stacked on any one of the two surfaces of the negative current collector.

If the positive electrode current collector is a metal current collector, the negative electrode current collector is the aforementioned composite current collector 10. If the positive electrode current collector is the aforementioned composite current collector 10, the negative electrode current collector can be the aforementioned composite current collector 10, or it can be a metal current collector, such as copper foil or copper alloy.

When the negative electrode current collector is the aforementioned composite current collector 10, it also has the corresponding beneficial effects as described above, which will not be repeated here.

The negative active material layer comprises a negative active material, and the negative active material includes graphite, such as at least one of natural graphite and artificial graphite.

The negative active material may also optionally comprise other negative active materials known in the art that can perform reversible ion intercalation/deintercalation.

Other negative active materials can be, for example, one or more of metallic lithium, mesophase carbon microspheres (MCMB for short), hard carbon, soft carbon, silicon, silicon-carbon composite, SiO, Li—Sn alloy, Li—Sn—O alloy, Sn, SnO, $SnO_2$, spinel structure lithium titanate and Li—Al allo.

Optionally, the mass percentage of graphite in the negative active material is more than 50 wt %, further more than 60 wt %, and still further more than 80 wt %. At this time, the low-temperature performance of the lithium-ion secondary battery in the embodiments of the present application can be more significantly improved.

The negative active material layer may also optionally comprise a conductive agent, and the type of the conductive agent is not limited in this application. As an example, the conductive agent is one or more of graphite, superconducting carbon, acetylene black, carbon black, Ketjen black, carbon dots, carbon nanotubes, graphene, and carbon nanofibers.

The negative active material layer may also optionally comprise a binder, and the type of binder is not limited in this application. As an example, the binder is one or more of styrene butadiene rubber (SBR), water-based acrylic resin, carboxymethyl cellulose (CMC), polyvinylidene fluoride (PVDF), polytetrafluoroethylene (PTFE), ethylene-vinyl acetate copolymer (EVA), polyvinyl alcohol (PVA) and polyvinyl butyral (PVB).

Preferably, the thickness $T_2$ of the negative active material layer is from 30 μm to 70 μm. If the thickness $T_2$ of the negative active material layer is within the above range, the effect of improving the low-temperature performance of the lithium-ion secondary battery is better, and at the same time, it can ensure that the negative electrode has good kinetic performance and improve the electrochemical performance of the lithium-ion secondary battery. More preferably, the thickness $T_2$ of the negative active material layer is 40 μm to 60 μm, which can further improve the low-temperature performance of the lithium-ion secondary battery, and obtain a negative electrode plate and a lithium-ion secondary battery with better comprehensive properties.

The aforementioned "thickness $T_2$ of the negative active material layer" refers to the thickness of the negative active material layer on one side of the negative electrode current collector.

The negative electrode plate can be prepared according to a conventional method in the art, such as a coating method. As an example, the negative active material and the optional conductive agent and binder are dispersed in a solvent which can be deionized water to form a uniform negative electrode slurry; the negative electrode slurry is coated on the negative electrode current collector and dried; after drying and other processes, a negative electrode plate is obtained.

Electrolytic Solution

An embodiment of the present application provides an electrolytic solution for a lithium-ion secondary battery. The electrolytic solution comprises an organic solvent and an electrolyte lithium salt dispersed in the organic solvent.

The organic solvent can be, for example, one or more of ethylene carbonate (EC), propylene carbonate (PC), pentylene carbonate, 1,2-butanediol carbonate (1,2-BC), 2,3-butanediol carbonate (2,3-BC), ethyl methyl carbonate (EMC), diethyl carbonate (DEC), dimethyl carbonate (DMC), dipropyl carbonate (DPC), methyl propyl carbonate (MPC), ethyl propyl carbonate (EPC), butene carbonate (BC), fluoroethylene carbonate (FEC), methyl formate (MF), ethyl formate (EM), methyl acetate (MA), ethyl acetate (EA), propyl acetate (PA), methyl propionate (MP), ethyl propionate (EP), propyl propionate (PP), methyl butyrate (MB), ethyl butyrate (EB), 1,4-butyrolactone (GBL), sulfolane (SF), methyl sulfone (MSM), ethyl methyl sulfone (EMS), and ethylsulfinylethane (ESE).

In some preferred embodiments, the organic solvent is a mixed solvent comprising cyclic carbonate and chain carbonate. Such organic solvents are conducive to preparing electrolytic solution with good comprehensive properties such as electrical conductivity and viscosity. Preferably, the conductivity of the electrolytic solution at 25° C. may be 8 mS/cm to 11 mS/cm. If the conductivity is too low, the kinetic performance of the electrolytic solution is relatively reduced, and the polarization of the lithium iron phosphate battery is relatively large, which affects the normal-temperature cycle performance and low-temperature performance; if the conductivity is too large, the thermal stability of the electrolytic solution is relatively reduced, which affects the high-temperature cycle performance of the lithium iron phosphate battery.

The electrolyte lithium salt may be, for example, one or more of $LiPF_6$ (lithium hexafluorophosphate), $LiBF_4$ (lithium tetrafluoroborate), $LiClO_4$ (lithium perchlorate), $LiAsF_6$ (lithium hexafluoroarsenate), LiFSI (lithium bisfluorosulfonimide), LiTFSI (lithium bistrifluoromethanesulfonimide), LiTFS (lithium trifluoromethanesulfonate), LiDFOB (lithium difluorooxalate borate), LiBOB (lithium dioxalate borate), $LiPO_2F_2$ (lithium difluorophosphate), LiDFOP (lithium difluorooxalatophosphate) and LiTFOP (lithium tetrafluorooxalate phosphate).

The electrolytic solution may optionally comprise an additive. The additive may comprise, for example, one or more of negative electrode film-forming additives, positive electrode film-forming additives, and additives that can improve certain performance of the battery, such as additives for improving overcharge performance of the battery, additives for improving high-temperature performance of the battery, and additives for improving low temperature-performance of the battery.

In some preferred embodiments, the additive comprises a cyclic carbonate containing an unsaturated bond, for example, a cyclic carbonate containing a double bond. The inclusion of a cyclic carbonate containing an unsaturated bond in the electrolytic solution can improve the capacity retention rate of lithium-ion secondary batteries using lithium iron phosphate as the positive active material during the storage and charge/discharge cycle in high-temperature environments, and improve the high-temperature performance of the lithium-ion secondary battery.

Further, the mass percentage of the cyclic carbonate containing an unsaturated bond in the electrolytic solution is preferably from 0.1% to 4%, more preferably from 0.5% to 4%, and more preferably from 0.5% to 3%.

In the lithium-ion secondary battery according to the embodiments of the present application, the content of the cyclic carbonate containing an unsaturated bond in the electrolytic solution is within the above range, which can form a solid electrolyte interface (SEI) film with good density and stability on the negative electrode, and the SEI film has good ion conductivity, which can improve the high-temperature cycle performance of the battery, can prevent the risk of lithium precipitation from the negative electrode during the cycle, and can improve the safety performance of the battery.

In some embodiments, the upper limit of the mass percentage of the cyclic carbonate containing an unsaturated bond in the electrolytic solution may be 4%, 3.8%, 3.5%, 3.2%, 3%, 2.8%, 2.5%, 2.2%, or 2.0%; the lower limit may be 0.1%, 0.5%, 0.7%, 0.8%, 0.9%, 1.0%, 1.2%, 1.4%, 1.5%, 1.7%, or 1.8%. The range of the mass percentage of the cyclic carbonate containing an unsaturated bond in the electrolytic solution can be formed by a combination of any of the foregoing upper limit with any of the foregoing lower limit, or can be formed by a combination of any upper limit and any other upper limit as described above, or can also be formed by a combination any lower limit with any other lower limit as described above.

Further, the above-mentioned cyclic carbonate containing an unsaturated bond can be selected from one or two of vinylene carbonate (VC) and vinyl ethylene carbonate (VEC).

In some preferred embodiments, the additive comprises a cyclic sulfonate, preferably a cyclic disulfonate represented by Formula I.

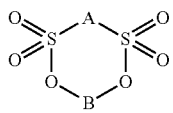

Formula I

In the above formula I, A and B are each independently selected from an alkylene group having 1 to 3 carbon atoms.

The inclusion of cyclic disulfonate in the electrolytic solution can reduce the SEI film impedance. Therefore, the low-temperature performance, normal-temperature performance and high-temperature cycle performance of the lithium-ion secondary battery using the lithium iron phosphate positive as the active material can be improved, and the battery life can be effectively extended.

Further, the mass percentage of the cyclic disulfonate in the electrolytic solution is preferably from 0.1% to 2%, more preferably from 0.2% to 2%, more preferably from 0.2% to 1%.

In the lithium-ion secondary battery according an the embodiment of the present application, the content of the cyclic disulfonate in the electrolytic solution is within the above range, which can effectively reduce the SEI film impedance, thereby effectively improving the low-temperature performance, room-temperature performance and high-temperature cycle performance of the lithium-ion secondary battery using lithium iron phosphate as the positive active material.

In some embodiments, the upper limit of the mass percentage of the cyclic disulfonate in the electrolytic solution may be 2%, 1.8%, 1.6%, 1.5%, 1.3%, 1.2%, 1.1%, 1.0%, 0.95%, or 0.9%; the lower limit may be 0.1%, 0.2%, 0.25%, 0.3%, 0.4%, 0.5%, 0.6%, 0.7%, 0.75%, 0.8%, or 0.85%. The range of the mass percentage of the cyclic disulfonate in the electrolytic solution can be formed by a combination of any of the foregoing upper limit and any lower limit, or can be formed by a combination of any of the foregoing upper limit and any other upper limit, It may also be formed by combining any of the aforementioned lower limit values and any other lower limit.

Further, the aforementioned cyclic disulfonate may be selected from one or more of methylene methane disulfonate (MMDS), ethylene ethane disulfonate (EEDS) and propylenemethane disulfonate (MPDS).

Separator

The embodiments of this application have no particular limitations on the types of separator, and any well-known porous structure separator with good chemical and mechanical stability can be selected, such as one or more of glass fiber, non-woven fabric, polyethylene, polypropylene and polyvinylidene fluoride. The separator can be a single-layer film or a multilayer composite film. When the separator is a multilayer composite film, the materials of each layer may be the same or different. The separator may also be a composite separator, for example, a composite separator provided with an inorganic coating on a surface of an organic separator.

Preferably, the porosity of the separator is 30%-50%, which can further improve the kinetic performance of the lithium-ion secondary battery and is beneficial to improving the low-temperature performance of the lithium-ion secondary battery.

Preparation of Lithium-Ion Secondary Battery

A positive electrode plate, a separator, and a negative electrode plate are stacked in order, so that the separator is located between the positive electrode plate and the negative electrode plate to serve as an isolation, so as to obtain a battery core, which can also be obtained after winding. The battery core is placed in a packaging case, and then an electrolytic solution is injected and sealed to obtain a lithium-ion secondary battery.

Example

The following examples are intended to describe the disclosure of the present application, and are intended to be illustrative only, and various modifications and changes in the scope of the present disclosure will be apparent to those skilled in the art. All parts, percentages, and ratios reported in the following examples are by weight unless otherwise stated, and all reagents used in the examples are commercially available or synthetically obtained by conventional methods and are directly used without further processing, and the instruments used in the examples are commercially available.

Preparation

Preparation of Conventional Positive Electrode Plate

The positive active material lithium iron phosphate (LFP), the binder polyvinylidene fluoride (PVDF), and the conductive agent acetylene black were mixed at a mass ratio of 98:1:1. Then N-methylpyrrolidone (NMP) as a solvent was added and the mixture was stirred uniformly with a vacuum stirrer to obtain a positive electrode slurry. The positive electrode slurry was evenly coated on an aluminum foil as a positive electrode current collector. After drying, cold pressing, and slitting, a conventional positive electrode plate was obtained. The compacted density of the positive electrode plate was 2.4 g/cm$^3$.

Preparation of Positive Electrode Plate

Different from the preparation of conventional positive electrode plate, the positive electrode current collector was a composite current collector, which was prepared by a vacuum evaporation method, including: selecting an organic support layer with a predetermined thickness and performing surface cleaning treatment; placing the organic support layer which was subjected to surface cleaning treatment in a vacuum plating chamber, and melting the high-purity aluminum wire in a metal evaporation chamber and evaporating at a high temperature of 1300° C.~2000° C.; passing the evaporated metal through the cooling system in the vacuum plating chamber and depositing it on the two surfaces of the organic support layer, forming a conductive layer.

Preparation of Conventional Negative Electrode Plate

The negative active material graphite, the conductive agent acetylene black, the thickener sodium carboxymethyl cellulose (CMC) solution and the binder styrene-butadiene rubber emulsion were mixed in the mass ratio of 97:1:1:1. Then deionized water as a solvent was added and the mixture was stirred uniformly under a vacuum stirrer to obtain a negative electrode slurry. The negative electrode slurry was evenly coated on a copper foil serving as a negative electrode current collector. After drying and cold pressing, a conventional negative electrode plate was obtained. The compacted density of the negative electrode plate was 1.7 g/cm$^3$.

Preparation of Negative Electrode Plate

Different from the preparation of conventional negative electrode plate, the negative electrode current collector was a composite current collector, which was prepared by a vacuum evaporation method, including: selecting an organic support layer with a predetermined thickness and performing surface cleaning treatment; placing the organic support layer which was subjected to surface cleaning treatment in a vacuum plating chamber, and melting the high-purity copper wire in a metal evaporation chamber and evaporating at a high temperature of 1300° C.~2000° C.; passing the evaporated metal through the cooling system in the vacuum plating chamber and depositing it on the two surfaces of the organic support layer, forming a conductive layer.

Preparation of Electrolytic Solution

The organic solvent was a mixed organic solvent of ethylene carbonate (EC), methyl ethyl carbonate (EMC), diethyl carbonate (DEC), dimethyl carbonate (DMC) and methyl propionate (MP). Lithium salt was $LiPF_6$, wherein the content of $LiPF_6$ was 12.5% by mass, based on the total mass of the electrolytic solution.

Preparation of Lithium-Ion Secondary Battery

The positive electrode plate, the negative electrode plate and the separator were wound to obtain a battery core, and the battery core was put into the packaging case, the electrolytic solution was injected and sealed. The lithium-ion secondary battery was obtained by the steps of standing, pressing, forming, degassing and the like.

Test Section (1) Test of Low-Temperature Performance of Lithium-Ion Secondary Battery At 25° C., the lithium-ion secondary battery was firstly discharged to 2.0V with a current of 1C; and then charged to 3.6V with a constant current of 1C, and then charged to a current of 0.05C with a constant voltage, at this time the charge capacity was represented by CC; and then the ambient temperature of the battery was adjusted to −10° C., and the battery was discharged to 2.0V with a constant current of 1C, at this time the discharge capacity was represented by CD. The ratio of discharge capacity CD to charge capacity CC was the discharge capacity retention of lithium-ion secondary battery at −10° C.

The discharge capacity retention (%) of lithium-ion secondary battery at −10° C.=CD/CC×100%.

(2) Test of High-Temperature Cycle Performance of Lithium-Ion Secondary Battery

At 25° C., the lithium-ion secondary battery was firstly discharged to 2.0V with a current of 1C, and then the ambient temperature of the battery was raised to 60° C. The battery was charged to 3.6V with a constant current of 1C, and then charged to the current of 0.05C with a constant voltage, and then discharged to 2.0V with a constant current of 1C. This was a charge and discharge cycle. The resulting discharge capacity was recorded as the discharge capacity for the first cycle. The lithium-ion secondary battery was subjected to a 500-cycle charge-discharge test following the procedure described above, and the discharge capacity for each cycle was recorded.

Capacity retention (%) of lithium-ion secondary battery for 500 cycles at 60° C.=the discharge capacity for the 500th cycle/the discharge capacity for the first cycle×100%.

Test Results

1. The Effect of Composite Current Collectors on Improving the Weight Energy Density of an Electrochemical Device 1) When the Positive Electrode Current Collector was a Composite Current Collector, its Effect on Improving the Weight Energy Density of the Electrochemical Device.

TABLE 1-1

| Positive electrode current collector No. | Organic support layer Material | $D_2$ (μm) | Conductive layer of positive Material | $D_1$ (μm) | Thickness of positive electrode current collector (μm) | Weight percentage of positive electrode current collector (%) |
|---|---|---|---|---|---|---|
| Positive electrode current collector 1 | PET | 10 | Al | 0.5 | 11.0 | 48.3 |
| Positive electrode current collector 2 | PI | 6 | Al | 0.3 | 6.6 | 30.0 |
| Positive electrode current collector 3 | PI | 5 | Al | 1.5 | 8.0 | 45.8 |
| Positive electrode current collector 4 | PET | 4 | Al | 0.9 | 5.8 | 31.0 |
| Positive electrode current collector 5 | PI | 3 | Al | 0.2 | 3.4 | 15.8 |
| Positive electrode current collector 6 | PI | 1 | Al | 0.4 | 1.8 | 10.9 |
| Conventional positive electrode current collector | / | / | Al | 12.0 | 12.0 | 100 |

In Table 1-1, the weight percentage of the positive electrode current collector referred to the weight of the positive electrode current collector per unit area divided by the weight of the conventional positive electrode current collector per unit area.

Compared with the conventional aluminum foil positive current collector, the weight of the positive current collector using the composite current collector was reduced to various degrees, thereby increasing the weight and energy density of the battery.

2) When the Negative Electrode Current Collector was a Composite Current Collector, its Effect on Improving the Weight Energy Density of the Electrochemical Device.

TABLE 1-2

| Negative electrode current collector No. | organic support layer material | $D_2$ (μm) | conductive layer material | $D_1$ (μm) | Thickness of negative electrode current collector (μm) | Weight percentage of negative electrode current collector (%) |
|---|---|---|---|---|---|---|
| Negative electrode current collector 1 | PET | 5 | Cu | 0.03 | 5.06 | 7 |
| Negative electrode current collector 2 | PET | 5 | Cu | 0.3 | 5.6 | 16 |
| Negative electrode current collector 3 | PET | 5 | Cu | 0.5 | 6 | 21.6 |
| Negative electrode current collector 4 | PET | 5 | Cu | 0.6 | 6.2 | 24.1 |
| Negative electrode current collector 5 | PI | 2 | Cu | 0.8 | 3.6 | 23.8 |
| Negative electrode current collector 6 | PET | 8 | Cu | 1 | 10 | 39.6 |
| Negative electrode current collector 7 | PET | 6 | Cu | 1.5 | 9 | 48.5 |
| Negative electrode current collector 8 | PET | 4 | Cu | 1.2 | 6.4 | 37.3 |
| Negative electrode current collector 9 | PET | 10 | Cu | 0.2 | 10.4 | 23.3 |
| Negative electrode current collector 10 | PI | 8 | Cu | 2 | 12 | 65.3 |
| Negative electrode current collector 11 | PET | 5 | Cu | 3 | 11 | 57.2 |
| Conventional negative electrode current collector | / | / | Cu | 8 | 8 | 100 |

In Table 1-2, the weight percentage of the negative electrode current collector was the weight of the negative electrode current collector per unit area divided by the weight of the conventional negative electrode current collector per unit area.

Compared with the conventional copper foil negative electrode current collector, the weight of the negative electrode current collector using the composite current collector was reduced to various degrees, thereby increasing the weight and energy density of the battery.

2. The Effect of Composite Current Collectors on the Electrochemical Performance of an Electrochemical Device

TABLE 2

| Battery No. | Positive electrode current collector | Positive active material | Negative electrode current collector | Negative active material | Discharge capacity retention at −10° C. (%) |
|---|---|---|---|---|---|
| Comparative battery | Conventional positive electrode current collector | LFP | Conventional negative electrode current collector | Graphite | 75 |
| Battery 1 | Conventional positive electrode current collector | LFP | Negative electrode current collector 6 | Graphite | 87 |
| Battery 2 | Conventional positive electrode current collector | LFP | Negative electrode current collector 8 | Graphite | 83 |
| Battery 3 | Positive electrode current collector 4 | LFP | Conventional negative electrode current collector | Graphite | 78 |
| Battery 4 | Positive electrode current collector 4 | LFP | Negative electrode current collector 6 | Graphite | 89 |

In the batteries in Table 2, the thickness of the negative active material layer was 52 μm, and the thickness of the positive active material layer was 74 μm.

The data in Table 2 showed that the use of composite current collectors could improve the low-temperature electrochemical performance of lithium-ion secondary battery using lithium iron phosphate.

3. The Thermal Conductivity of the Composite Current Collector and the Effect Thereof on the Low-Temperature Electrochemical Performance of an Electrochemical Device

TABLE 3-1

| Positive electrode current collector No. | Organic support layer Material | $D_2$ (μm) | Conductive layer Material | $D_1$ (μm) | F (N/m) | Thermal Conductivity (W/(m·K)) |
|---|---|---|---|---|---|---|
| Positive electrode current collector 31 | PET | 8 | Al | 0.4 | >100 N/m | 0.2 |
| Positive electrode current collector 32 | PET | 6 | Al | 0.6 | >100 N/m | 1 |
| Positive electrode current collector 4 | PET | 4 | Al | 0.9 | >100 N/m | 1.4 |
| Positive electrode current collector 33 | PET | 6 | Al | 1.0 | >100 N/m | 1.5 |
| Conventional positive electrode current collector | / | / | Al | 12 | / | 218 |
| Negative electrode current collector 31 | PET | 16 | Cu | 0.2 | >100 N/m | 0.01 |

TABLE 3-1-continued

| Positive electrode current collector No. | Organic support layer Material | $D_2$ (μm) | Conductive layer Material | $D_1$ (μm) | F (N/m) | Thermal Conductivity (W/(m·K)) |
|---|---|---|---|---|---|---|
| Negative electrode current collector 32 | PET | 8 | Cu | 0.4 | >100 N/m | 0.1 |
| Negative electrode current collector 33 | PET | 4 | Cu | 0.6 | >100 N/m | 0.5 |
| Negative electrode current collector 6 | PET | 8 | Cu | 1.0 | >100 N/m | 0.3 |
| Negative electrode current collector 34 | PET | 4 | Cu | 1.0 | >100 N/m | 1 |
| Negative electrode current collector 8 | PET | 4 | Cu | 1.2 | >100 N/m | 1.2 |
| Negative electrode current collector 35 | PET | 4 | Cu | 2.0 | >100 N/m | 2 |
| Negative electrode current collector 36 | PET | 2 | Cu | 3.0 | >100 N/m | 10 |
| Conventional negative electrode current collector | / | / | Cu | 8 | / | 381 |

TABLE 3-2

| No. of battery | Positive electrode current collector | Positive active material | Negative electrode current collector | Negative active material | Discharge capacity retention at −10° C. (%) |
|---|---|---|---|---|---|
| Comparative battery 1 | Conventional positive electrode current collector | LFP | Conventional negative electrode current collector | Graphite | 75 |
| Battery 1 | Conventional positive electrode current collector | LFP | Negative electrode current collector 31 | Graphite | 92 |
| Battery 2 | Conventional positive electrode current collector | LFP | Negative electrode current collector 32 | Graphite | 89 |
| Battery 3 | Conventional positive electrode current collector | LFP | Negative electrode current collector 33 | Graphite | 87 |
| Battery 4 | Conventional positive electrode current collector | LFP | Negative electrode current collector 34 | Graphite | 84 |
| Battery 5 | Conventional positive electrode current collector | LFP | Negative electrode current collector 35 | Graphite | 81 |
| Battery 6 | Conventional positive electrode current collector | LFP | Negative electrode current collector 36 | Graphite | 78 |
| Battery 7 | Positive electrode current collector 31 | LFP | Conventional negative electrode current collector | Graphite | 88 |
| Battery 8 | Positive electrode current collector 32 | LFP | Conventional negative electrode current collector | Graphite | 83 |
| Battery 9 | Positive electrode current collector 33 | LFP | Conventional negative electrode current collector | Graphite | 82 |

In the batteries in Table 3-2, the thickness of the negative active material layer was 52 μm, and the thickness of the positive active material layer was 74 μm.

As can be seen from the data in Table 3-2, the thermal conductivity of the composite current collector was 0.01 W/(m·K)~10 W/(m·K), which could improve the low-temperature performance of lithium iron phosphate batteries.

4. The Effect of Additive for Electrolytic Solution on the Electrochemical Performance of an Electrochemical Device

TABLE 4

| No. of battery | Negative electrode current collector | Additive for electrolytic solution | Capacity retention at −10° C. (%) | Capacity retention (%) after 500 cycles at 60° C. (%) |
|---|---|---|---|---|
| Comparative battery 1 | Conventional negative electrode current collector | / | 75 | 90 |
| Battery 4 | Negative electrode current collector 34 | / | 84 | 88 |
| Battery 41 | Negative electrode current collector 34 | VC 0.5 wt % | 88 | 91 |
| Battery 42 | Negative electrode current collector 34 | VC 4 wt % | 85 | 89 |
| Battery 43 | Negative electrode current collector 34 | MMDS 0.2 wt % | 90 | 92 |
| Battery 44 | Negative electrode current collector 34 | MMDS 2 wt % | 86 | 90 |
| Battery 45 | Negative electrode current collector 34 | VC 1 wt %; MMDS 1 wt % | 92 | 93 |

In the batteries in Table 4, all the positive electrode current collectors were conventional positive current collectors, and all the positive active materials of the positive active material layer were LFP, and the thickness of the positive active material layer was 74 μm; all the negative active materials of the negative active material layer were graphite, and the thickness of the negative active material layer was 52 μm; the content of the additive for electrolytic solution referred to the mass percentage of the additive in the electrolytic solution.

As can be seen from the data in Table 4, the addition of a cyclic carbonate containing an unsaturated bond and/or a cyclic disulfonate to the electrolytic solution could further improve the low-temperature performance and high-temperature cycle performance of the lithium-ion secondary battery.

5. The Effect of the Thickness of the Active Material Layer of the Electrode Plate on the Low-Temperature Performance of an Electrochemical Device In the batteries in Table 5, all the positive active materials of the positive active material layer were LFP, and all the negative active material of the negative active material layer were graphite.

As can be seen from the data in Table 5, when the thickness $T_1$ of the positive active material layer was 50 nm~100 nm, the present application had a better effect on improving the low-temperature performance of the lithium-ion secondary battery; further, when the thickness $T_1$ of the positive active material layer was 60 nm~90 nm, the low-temperature performance of the lithium-ion secondary battery was further improved. When the thickness $T_2$ of the negative active material layer was 30 nm~70 nm, the present application had a better effect on improving the low-tem-

TABLE 5

| No. of battery | Positive electrode current collector | Thickness of positive active material layer (μm) | Negative electrode current collector | Thickness of negative active material layer (μm) | Discharge capacity retention at −10° C. (%) |
|---|---|---|---|---|---|
| Comparative battery 2 | Conventional positive electrode current collector | 110 | Negative electrode current collector 34 | 52 | 73 |
| Battery 4 | Conventional positive electrode current collector | 74 | Negative electrode current collector 34 | 52 | 84 |
| Battery 51 | Conventional positive electrode current collector | 50 | Negative electrode current collector 34 | 52 | 81 |
| Battery 52 | Conventional positive electrode current collector | 60 | Negative electrode current collector 34 | 52 | 83 |
| Battery 53 | Conventional positive electrode current collector | 90 | Negative electrode current collector 34 | 52 | 82 |
| Battery 54 | Conventional positive electrode current collector | 100 | Negative electrode current collector 34 | 52 | 79 |
| Battery 55 | Conventional positive electrode current collector | 74 | Negative electrode current collector 34 | 30 | 77 |
| Battery 56 | Conventional positive electrode current collector | 74 | Negative electrode current collector 34 | 40 | 82 |
| Battery 57 | Conventional positive electrode current collector | 74 | Negative electrode current collector 34 | 60 | 83 |
| Battery 58 | Conventional positive electrode current collector | 74 | Negative electrode current collector 34 | 70 | 80 |
| Comparative battery 3 | Conventional positive electrode current collector | 74 | Negative electrode current collector 34 | 85 | 75 | perature performance of the lithium-ion secondary battery; further, when the thickness $T_2$ of the negative active material layer was 40 nm~60 nm, the low-temperature performance of the lithium-ion secondary battery could be further improved.

6. The Effect of the Protective Layer on the Low-Temperature Performance of an Electrochemical Device

TABLE 6-1

| No. of positive electrode current collector | Upper protective layer | | Lower protective layer | |
|---|---|---|---|---|
| | Material | $D_a$ (nm) | Material | $D_b$ (nm) |
| Positive electrode current collector 33-1 | / | / | Nickel | 1 |
| Positive electrode current collector 33-2 | / | / | Nickel oxide | 50 |
| Positive electrode current collector 33-3 | Nickel oxide | 5 | / | / |
| Positive electrode current collector 33-4 | Nickel oxide | 10 | / | / |
| Positive electrode current collector 33-5 | Nickel oxide | 50 | Nickel oxide | 50 |
| Positive electrode current collector 33-6 | Nickel oxide | 100 | Nickel oxide | 50 |

In Table 6-1, a protective layer was disposed on the basis of the positive electrode current collector 33.

TABLE 6-2

| No. of battery | Positive electrode current collector | Positive active material | Negative electrode current collector | Negative active material | Capacity retention (%) after 500 cycles at 60° C. (%) |
|---|---|---|---|---|---|
| Battery 62 | Positive electrode current collector 33 | LFP | Negative electrode current collector 34 | Graphite | 86 |
| Battery 62-1 | Positive electrode current collector 33-1 | LFP | Negative electrode current collector 34 | Graphite | 87 |
| Battery 62-2 | Positive electrode current collector 33-2 | LFP | Negative electrode current collector 34 | Graphite | 88 |
| Battery 62-3 | Positive electrode current collector 33-3 | LFP | Negative electrode current collector 34 | Graphite | 87 |
| Battery 62-4 | Positive electrode current collector 33-4 | LFP | Negative electrode current collector 34 | Graphite | 88 |
| Battery 62-5 | Positive electrode current collector 33-5 | LFP | Negative electrode current collector 34 | Graphite | 90 |
| Battery 62-6 | Positive electrode current collector 33-6 | LFP | Negative electrode current collector 34 | Graphite | 91 |

In the batteries in Table 6-2, the thickness of the negative active material layer was 52 μm, and the thickness of the positive active material layer was 74 μm.

As can be seen from the data in Table 6-2, when the positive electrode current collector was a composite current collector, the protective layer could further improve the capacity retention rate of the battery after 500 cycles at 60° C. and 1C/1C, and the battery reliability was better.

TABLE 6-3

| No. of negative electrode current collector | Upper protective layer | | Lower protective layer | |
|---|---|---|---|---|
| | Material | $D_a$ (nm) | Material | $D_b$ (nm) |
| Negative electrode current collector 35-1 | / | / | Nickel oxide | 1 |
| Negative electrode current collector 35-2 | / | / | Nickel-based alloy | 50 |
| Negative electrode current collector 35-3 | Nickel | 5 | / | / |
| Negative electrode current collector 35-4 | Nickel | 10 | / | / |
| Negative electrode current collector 35-5 | Nickel | 50 | Nickel | 50 |
| Negative electrode current collector 35-6 | Nickel | 100 | Nickel | 50 |
| Negative electrode current collector 35-7 | Double protective layers | 60 | Nickel | 50 |

In Table 6-3, a protective layer was disposed on the basis of the negative electrode current collector 35.

The nickel-based alloy in Table 6-3 contained: nickel, 90 wt %; chromium, 10 wt %.

The double protective layers in Table 6-3 include a nickel protective layer disposed on the surface of the conductive layer facing away from the organic support layer, with a thickness of 30 nm; and a nickel oxide protective layer disposed on the surface of the nickel protective layer facing away from the organic support layer, with a thickness of 30 nm.

TABLE 6-4

| No. of battery | Positive electrode current collector | Positive active material | Negative electrode current collector | Negative active material | Capacity retention (%) after 500 cycles at 60° C. (%) |
|---|---|---|---|---|---|
| Battery 64 | Conventional positive electrode current collector | LFP | Negative electrode current collector 35 | Graphite | 90 |
| Battery 64-1 | Conventional positive electrode current collector | LFP | Negative electrode current collector 35-1 | Graphite | 91 |
| Battery 64-2 | Conventional positive electrode current collector | LFP | Negative electrode current collector 35-2 | Graphite | 92 |
| Battery 64-3 | Conventional positive electrode current collector | LFP | Negative electrode current collector 35-3 | Graphite | 91 |
| Battery 64-4 | Conventional positive electrode current collector | LFP | Negative electrode current collector 35-4 | Graphite | 92 |
| Battery 64-5 | Conventional positive electrode current collector | LFP | Negative electrode current collector 35-5 | Graphite | 93 |
| Battery 64-6 | Conventional positive electrode current collector | LFP | Negative electrode current collector 35-6 | Graphite | 94 |

TABLE 6-4-continued

| No. of battery | Positive electrode current collector | Positive active material | Negative electrode current collector | Negative active material | Capacity retention (%) after 500 cycles at 60° C. (%) |
|---|---|---|---|---|---|
| Battery 64-7 | Conventional positive electrode current collector | LFP | Negative electrode current collector 35-7 | Graphite | 93 |

In the batteries in Table 6-4, the thickness of the negative active material layer was 52 μm, and the thickness of the positive active material layer was 74 μm.

As can be seen from the data in Table 6-4, when the negative electrode current collector was a composite current collector, the protective layer could further improve the capacity retention rate of the battery after 500 cycles at 60° C. and 1C/1C, and the battery reliability was better.

The above mentioned descriptions only show particular implementations of the present application and but are not intended to limit the protection scope of the present application. Any modification or replacement readily figured out by a person skilled in the art within the technical scope disclosed in the present application shall fall within the protection scope of the present application. Therefore, the protection scope of the present application shall be determined by the protection scope of the claims.

What is claimed is:

1. A lithium-ion secondary battery comprising a positive electrode plate, a negative electrode plate, a separator, and an electrolytic solution, wherein the positive electrode plate comprises a positive electrode current collector and a positive active material layer disposed on a surface of the positive electrode current collector and containing a positive active material, and the negative electrode plate comprises a negative electrode current collector and a negative active material layer disposed on a surface of the negative electrode current collector and containing a negative active material;
wherein the positive active material comprises lithium iron phosphate, and the negative active material comprises graphite;
wherein the positive electrode current collector and/or the negative electrode current collector are composite current collector, and the composite current collector comprises an organic support layer and a conductive layer disposed on at least one surface of the organic support layer;
wherein the conductive layer has a thickness $D_1$ of 300 nm<$D_1$<2 μm and the organic support layer has a thickness $D_2$ of 1 μm<$D_2$<30 μm; and
wherein the composite current collector has a thermal conductivity of 0.01 W/(m·K)~2 W/(m·K).

2. The lithium-ion secondary battery according to claim 1, wherein the positive electrode current collector is a metal current collector or the composite current collector, and the negative electrode current collector is the composite current collector.

3. The lithium-ion secondary battery according to claim 1, wherein
the positive active material layer has a thickness $T_1$ satisfying 50 μm<$T_1$<100 μm, and the negative active material layer has a thickness $T_2$ satisfying 30 μm<T2<70 μm; and/or, the electrolytic solution comprises an organic solvent which is a mixed solvent comprising a cyclic carbonate and a chain carbonate, and the electrolytic solution has a conductivity at 25° C. of 8 mS/cm·11 mS/cm; and/or, the separator has a porosity of 30%-50%.

4. The lithium-ion secondary battery according to claim 1, wherein the organic support layer has a thickness $D_2$ of 1 μm<$D_2$<15 μm.

5. The lithium-ion secondary battery according to claim 1, wherein the positive active material layer has a thickness $T_1$ satisfying 60 μm<$T_1$<90 μm.

6. The lithium-ion secondary battery according to claim 1, wherein the negative active material layer has a thickness $T_2$ satisfying 40 μm<T2<60 μm.

7. The lithium-ion secondary battery according to claim 1, wherein the electrolytic solution comprises a cyclic carbonate containing an unsaturated bond, and the cyclic carbonate containing an unsaturated bond is present in an amount of 0.5%~4% by mass in the electrolytic solution.

8. The lithium-ion secondary battery according to claim 7, wherein the cyclic carbonate containing an unsaturated bond comprises one or two of vinylene carbonate VC and vinyl ethylene carbonate VEC.

9. The lithium-ion secondary battery according to claim 1, wherein the electrolytic solution comprises a cyclic disulfonate represented by formula I, and the cyclic disulfonate is present in an amount of 0.2%~2% by mass in the electrolytic solution;

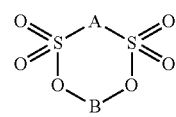

Formula I in the above formula I, A and B are each independently selected from an alkylene group having 1 to 3 carbon atoms.

10. The lithium-ion secondary battery according to claim 9, wherein the cyclic disulfonate comprises one or more of methylene methane disulfonate, ethylene ethane disulfonate and propylene methane disulfonate.

11. The lithium-ion secondary battery according to claim 7, wherein the electrolytic solution comprises a cyclic disulfonate represented by formula I, and the cyclic disulfonate is present in an amount of 0.2%~2% by mass in the electrolytic solution;

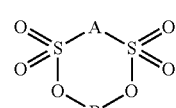

Formula I in the above formula I, A and B are each independently selected from an alkylene group having 1 to 3 carbon atoms.

12. The lithium-ion secondary battery according to claim 11, wherein the cyclic disulfonate comprises one or more of methylene methane disulfonate, ethylene ethane disulfonate and propylene methane disulfonate.

13. The lithium-ion secondary battery according to claim 1, wherein:
the organic support layer has a Young's modulus E of E>2 GPa; and/or,
there is a bonding force F between the organic support layer and the conductive layer, which satisfies F>100 N/m; and/or,
the organic support layer comprises one or more of polymer material and polymer-based composite material, wherein the polymer material is one or more of polyamide, polyimide, polyethylene terephthalate, polybutylene terephthalate, polyethylene naphthalate, polycarbonate, polyethylene, polypropylene, poly(propylene-ethylene), acrylonitrile-butadiene-styrene copolymer, polyvinyl alcohol, polystyrene, poly vinyl chloride, polyvinylidene fluoride, polytetrafluoroethylene, sodium polystyrene sulfonate, polyacetylene, silicone rubber, polyoxymethylene, polyphenylene oxide, polyphenylene sulfide, polyethylene glycol, polysulfur nitride, polyphenylene, polypyrrole, polyaniline, polythiophene, polypyridine, cellulose, starch, protein, epoxy resin, phenolic resin, the derivatives thereof, the cross-linked products thereof, and the copolymers thereof, and wherein the polymer-based composite material comprises the polymer material and an additive comprising one or more of metallic materials and inorganic nonmetallic materials.

14. The lithium-ion secondary battery according to claim 1, wherein:
the conductive layer comprises one or more of metal material, carbon-based conductive material and conductive polymer material; and/or,
the conductive layer has a volume resistivity of less than or equal to $8.0 \times 10^{-8}$ Ω·m.

15. The lithium-ion secondary battery according to claim 1, wherein the composite current collector further comprises a protective layer, and the protective layer is disposed on at least one of two opposite surfaces of the conductive layer in the thickness direction; and
wherein the protective layer comprises one or more of metal, metal oxide, and conductive carbon.

16. The lithium-ion secondary battery according to claim 15, wherein the protective layer comprises one or more of nickel, chromium, nickel-based alloy, copper-based alloy, aluminum oxide, cobalt oxide, chromium oxide, nickel oxide, graphite, super conductive carbon, carbon black, carbon dots, carbon nanotubes, graphene and carbon nanofibers.

17. The lithium-ion secondary battery according to claim 15, wherein the protective layer has a thickness $D_3$ of 1 nm<$D_3$<200 nm, and the thickness $D_3$ of the protective layer and the thickness $D_1$ of the conductive layer satisfy $D_3$<$0.1D_1$.

18. The lithium-ion secondary battery according to claim 15, wherein when the composite current collector is a negative electrode current collector, the composite current collector comprises an upper protective layer disposed on the surface of the conductive layer facing away from the organic support layer, and wherein the upper protective layer comprises:
a metal protective layer disposed on the surface of the conductive layer facing away from the organic support layer; and
a metal oxide protective layer disposed on the surface of the metal protective layer facing away from the organic support layer.

* * * * *